(12) United States Patent
Robert et al.

(10) Patent No.: US 10,098,832 B1
(45) Date of Patent: Oct. 16, 2018

(54) COMPOSITIONS FOR SHORT AND LONG TERM BENEFITS FOR MINIMIZING WRINKLES AND FINE LINES

(71) Applicant: L'OREAL, Paris (FR)

(72) Inventors: Valerie A. Robert, Scotch Plains, NJ (US); Geoffrey David Genesky, New York, NY (US); Nariyoshi Yoshioka, Shanghai (CN)

(73) Assignee: L'Oreal, Paris (FR)

( * ) Notice: Subject to any disclaimer, the term of this patent is extended or adjusted under 35 U.S.C. 154(b) by 67 days.

(21) Appl. No.: 15/475,350

(22) Filed: Mar. 31, 2017

(51) Int. Cl.
| | |
|---|---|
| *A61K 8/894* | (2006.01) |
| *A61K 8/97* | (2017.01) |
| *A61K 8/34* | (2006.01) |
| *A61K 8/67* | (2006.01) |
| *A61K 8/73* | (2006.01) |
| *A61K 8/49* | (2006.01) |
| *A61K 8/891* | (2006.01) |
| *A61K 8/89* | (2006.01) |
| *A61Q 19/08* | (2006.01) |
| *A61K 8/06* | (2006.01) |
| *A61K 8/37* | (2006.01) |

(52) U.S. Cl.
CPC ............ *A61K 8/894* (2013.01); *A61K 8/06* (2013.01); *A61K 8/345* (2013.01); *A61K 8/37* (2013.01); *A61K 8/494* (2013.01); *A61K 8/676* (2013.01); *A61K 8/735* (2013.01); *A61K 8/89* (2013.01); *A61K 8/891* (2013.01); *A61K 8/97* (2013.01); *A61Q 19/08* (2013.01)

(58) Field of Classification Search
None
See application file for complete search history.

(56) References Cited

U.S. PATENT DOCUMENTS

| | | |
|---|---|---|
| 2006/0280711 A1 | 12/2006 | Cornell et al. |
| 2009/0075935 A1 | 3/2009 | Bissey et al. |
| 2013/0236571 A1 | 9/2013 | Magdassi et al. |

FOREIGN PATENT DOCUMENTS

| | | |
|---|---|---|
| EP | 2123257 A3 | 11/2009 |
| WO | 200002535 | 1/2000 |
| WO | 2006072243 A1 | 7/2006 |
| WO | 2009030372 A1 | 3/2009 |
| WO | 2009112492 A2 | 9/2009 |

OTHER PUBLICATIONS

International Search Report for PCT/US2018/024770 dated Jun. 25, 2018.

*Primary Examiner* — Jeffrey T. Palenik
(74) *Attorney, Agent, or Firm* — McNees Wallace & Nurick

(57) ABSTRACT

The present invention relates to a cosmetic composition including an oil phase, a polyol phase, and a phase. The oil phase includes polysilicone-11, mixture of dimethicone, dimethicone crosspolymer and cetyl peg/ppg-10/1 dimethicone, ethylhexyl palmitate; and hyaluronic acid derivative. The polyol phase includes ascorbic acid, ascorbyl glucoside, propylene glycol, glycerin, and hydroxyethylpiperazine ethane sulfonic acid. The tertiary phase includes anogeissus leiocarpus bark extract. The cosmetic composition provides immediate soft focus effect and long term anti-wrinkle effect. The present invention also relates to a method of making the cosmetic composition.

18 Claims, No Drawings

COMPOSITIONS FOR SHORT AND LONG TERM BENEFITS FOR MINIMIZING WRINKLES AND FINE LINES

FIELD OF THE INVENTION

The present invention relates to cosmetic compositions for treating anti-age and method of making them. More particularly, the present invention relates to cosmetic compositions for treating wrinkles and fine lines on a short-term basis and long-term basis, the compositions including ascorbic acid derivatives, hyaluronic acid derivatives, polysilicone-11, humectants, mixture of silicone, silicone cross polymer, silicone surfactant and acid ester, and anti-aging ingredients.

BACKGROUND OF THE INVENTION

Ascorbic acid derivatives are important to skin but are difficult to stabilize in formula, particularly at high concentration for maximum activity. Conventional cosmetic compositions generally keep concentration of ascorbic acid derivatives low to avoid any instability of the acids. Cosmetic products with high concentrated, solubilized, and stable ascorbic acid derivatives along with other beneficial components are especially desired by consumers because of long-term therapeutic benefits such as diminishing wrinkles and reducing fine lines.

Today's consumers also desire cosmetic products that prove immediate skin benefits such as refining texture for smoother skin, brightening the overall appearance of skin, and reducing the appearance of fine lines.

It is thus an object of the present invention to provide cosmetic products with highly concentrated, soluble, and stable ascorbic acids and other beneficial components to provide customers with both short-term and long-term skin benefits.

Accordingly, another object of this position is to provide a method of making cosmetic products that are capable of providing both short-term and long-term skin benefits.

BRIEF SUMMARY OF THE INVENTION

In an exemplary embodiment, a cosmetic composition comprising an oil phase, a polyol phase, and an optional tertiary phase is provided. The oil phase includes polysilicone-11, mixture of dimethicone, dimethicone crosspolymer and cetyl peg/ppg-10/1 dimethicone, ethylhexyl palmitate; and hyaluronic acid derivative. The polyol phase includes ascorbic acid, ascorbyl glucoside, propylene glycol, glycerin, and hydroxyethylpiperazine ethane sulfonic acid. The optional tertiary phase includes anogeissus leiocarpus bark extract. The cosmetic composition provides immediate soft focus effect and long term anti-wrinkle effect.

In another exemplary embodiment, a cosmetic composition comprising an oil phase, a polyol phase, and an optional tertiary phase is provided. The oil phase includes 0.1-5.0 wt % of polysilicone-11, 18-42 wt % of mixture of dimethicone, dimethicone crosspolymer and cetyl peg/ppg-10/1 dimethicone, 1.0-5.0 wt % of ethylhexyl palmitate; and 0.01-1.0 wt % of hyaluronic acid derivative. The polyol phase includes 0.1-20 wt % of ascorbic acid, 0.1-5.0 wt % of ascorbyl glucoside, 0.1-60 wt % of propylene glycol, 0.1-60 wt % of glycerin, and 0.1-5.0 wt % of hydroxyethylpiperazine ethane sulfonic acid. The optional tertiary phase includes 0.1-5.0 wt % of anogeissus leiocarpus bark extract. The cosmetic composition provides immediate soft focus effect and long term anti-wrinkle effect.

In another exemplary embodiment, a method of making a cosmetic composition is provided. The method includes the step of preparing an oil phase by mixing polysilicone-11, mixture of dimethicone, dimethicone crosspolymer and cetyl peg/ppg-10/1 dimethicone, ethylhexyl palmitate, and hyaluronic acid derivative. The method further includes the step of preparing a polyol phase by heating and dissolving ascorbic acid, ascorbyl glucoside, propylene glycol, glycerin, and hydroxyethylpiperazine ethane sulfonic acid at 85° C. The method further includes the step of cooling the polyol phase. The method further includes the step of mixing the oil phase and polyol phase. The method optionally further includes the step of adding an anogeissus leiocarpus bark extract to the mixture of the oil phase and polyol phase.

Other features and advantages of the present invention will be apparent from the following more detailed description, taken in conjunction with the accompanying drawings which illustrate, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The term "comprising" (and its grammatical variations) as used herein is used in the inclusive sense of "having" or "including" and not in the exclusive sense of the terms "consisting only of," "consisting essentially of" and "consisting of."

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient.

Applicants have surprisingly discovered that combination of ascorbic acid derivatives, hyaluronic acid derivatives, polysilicone-11, humectants, mixture of silicone, silicone cross polymer, silicone surfactant and acid ester, and anti-aging ingredients with specific and unique ratios among them yields a stable composition, thereby providing both short-term and long-term skin benefits. Short term skin benefits include refining texture for smoother skin, brightening the overall appearance of skin, and reducing the appearance of fine lines. Long-term skin benefits include reducing the appearance of fine lines, and diminishing deep wrinkles.

In some embodiments, in accordance with the invention, the ratio of (1) glycerin and the (2) mixture of dimethicone, dimethicone crosspolymer, and cetyl peg/ppg-10/1 is from 1:0.9 to 1:3.6, the ratio of the (2) mixture of dimethicone, dimethicone crosspolymer, and cetyl peg/ppg-10/1 and (3) ethylhexyl palmitate is from 3.6:1 to 8.4:1, and the ratio of (1) glycerin and (3) ethylhexyl palmitate is from 1:1 to 5:1, wherein the ratio of glycerin and the mixture of dimethicone, dimethicone crosspolymer, and cetyl peg/ppg-10/1 excludes 1:1.5, and wherein the ratio of glycerin and ethylhexyl palmitate excludes 2.5:1.

The cosmetic composition according to the present disclosure includes oil phase, polyol phase, and tertiary phase.

Oil Phase

The oil phase present in the cosmetic composition, according to the disclosure, includes polysilicone-11, mixture of dimethicone crosspolymer and cetyl peg/ppeg-10/1 dimethicone, ethylhexyl palmitate, and hyaluronic acid derivative. Hyaluronic acid derivative is expected to provide biological effects for anti-wrinkles and anti-fine lines.

In accordance with various embodiment, specific mixture of (1) dimethicone, (2) dimethicone cross polymer, (3) cetyl peg/ppg-10/1 dimethicone, wherein ratio is from about 4:7:1 to about 5:8:1 based upon weight, including increments and ranges there between, yields high concentrated, soluble, and stable ascorbic acid derivatives in the combination. On the other hand, polysilicone-11 is expected to provide instant haze effect.

In some embodiments, the oil phase includes from about 0.1 to about 5.0 wt % of polysilicone-11, from about 18 to about 42 wt % of mixture of dimethicone, dimethicone crosspolymer and cetyl peg/ppg-10/1 dimethicone, from about 1.0 to about 5.0 wt % of ethylhexyl palmitate; and from about 0.01 to about 1.0 wt % of hyaluronic acid derivative, including increments and ranges there between.

Polyol Phase

The polyol phase present in the cosmetic composition, according to the disclosure, includes ascorbic acid, ascorbyl glucoside, propylene glycol, glycerin, and hydroxyethylpiperazine ethane sulfonic acid. Ascorbic acid, ascorbyl glucoside, and hydroxyethylpiperazine ethane sulfonic acid are expected to provide biological effects for anti-wrinkles and anti-fine lines.

In some embodiments, the polyol phase includes from about 0.1 to about 20 wt % of ascorbic acid, from about 0.1 to about 5.0 wt % of ascorbyl glucoside, from about 0.1 to about 60 wt % of propylene glycol, from about 0.1 to about 60 wt % of glycerin, and from about 0.1 to about 5.0 wt % of hydroxyethylpiperazine ethane sulfonic acid, including increments and ranges there between.

Optional Tertiary Phase

The optional tertiary phase present in the cosmetic composition, according to the disclosure, includes anogeissus leiocarpus bark extract or one or more other additives and extracts, wherein such additive or extract expected to provide biological effects for anti-wrinkles and anti-fine lines.

In some embodiments, the tertiary phase includes from about 0.1 to about 5.0 wt % of the additive or extract such as anogeissus leiocarpus bark extract, including increments and ranges there between.

Optionally included in one of the oil or polyol or optional tertiary phases are one or more cosmetically acceptable additives selected from antioxidants, free-radical scavengers, vitamins, anti-elastase and anti-collagenase agents, peptides, steroids, trace elements, extracts of algae and of planktons, enzymes and coenzymes, flavonoids and ceramides, hydroxy acids, essential oils, fragrances, preservatives, bactericides, tocopherol, retinol, capryloyl salicylic acid, botanical extracts, and combinations thereof.

Method

The cosmetic composition is prepared by combining an oil phase, polyol phase, and tertiary phase. The method includes the step of mixing polysilicone-11, mixture of dimethicone, dimethicone crosspolymer and cetyl peg/ppg-10/1 dimethicone, ethylhexyl palmitate, and hyaluronic acid derivative. The method further includes the step of preparing a polyol phase by heating and dissolving ascorbic acid, ascorbyl glucoside, propylene glycol, glycerin, and hydroxyethylpiperazine ethane sulfonic acid at 85° C. The method further includes the step of cooling the polyol phase. The method further includes the step of mixing the oil phase and polyol phase. The method further includes the optional step of adding an anogeissus leiocarpus bark extract to the mixture of the oil phase and polyol phase.

The following examples are intended to further illustrate the present invention. They are not intended to limit the invention in any way. Unless otherwise indicated, all parts are by weight.

The inventive formulations were made generally in accordance with the method described above. As further described herein below, the inventive formulations were evaluated in terms of appearance, viscosity, stability, and soft focus effect.

TABLE 1

| Formulas | Inventive Example 1 | Inventive Example 2 | Inventive Example 3 | Inventive Example 4 |
|---|---|---|---|---|
| POLYSILICONE-11 | 2 | 2 | 2 | 2 |
| DIMETHICONE; 5cs | 6 | 14 | 6 | 6 |
| DIMETHICONE CROSSPOLYMER; DOW CORNING EL-9240 SILICONE ELASTOMER BLEND 2cs | 10.5 | 24.5 | 10.5 | 10.5 |
| CETYL PEG/PPG-10/1 DIMETHICONE; ABIL EM90 | 1.5 | 3.5 | 1.5 | 1.5 |

TABLE 1-continued

Inventive cosmetic composition

| Formulas | Inventive Example 1 | Inventive Example 2 | Inventive Example 3 | Inventive Example 4 |
| --- | --- | --- | --- | --- |
| ETHYLHEXYL PALMITATE | 5 | 5 | 2.5 | 2.5 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 54.3 | 15.3 | 49.3 | 56.8 |
| GLYCERIN | 5 | 20 | 12.5 | 5 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 5 | 4 | 5 | 5 |
| Viscosity | 5 | 5 | 4 | 4 |
| Stability | 5 | 5 | 5 | 5 |
| Soft focus effect | n/a | n/a | n/a | n/a |

TABLE 2

Inventive cosmetic composition

| Formulas | Inventive Example 5 | Inventive Example 6 | Inventive Example 7 | Inventive Example 8 |
| --- | --- | --- | --- | --- |
| POLYSILICONE-11 | 2 | 2 | 2 | 2 |
| DIMETHICONE; 5cs | 11 | 6 | 6 | 11 |
| DIMETHICONE CROSSPOLYMER; DOW CORNING EL-9240 SILICONE ELASTOMER BLEND 2cs | 19 | 10.5 | 10.5 | 19 |
| CETYL PEG/PPG-10/1 DIMETHICONE; ABIL EM90 | 2.7 | 1.5 | 1.5 | 2.7 |
| ETHYLHEXYL PALMITATE | 4 | 5 | 5 | 4 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 30.6 | 54.3 | 41.3 | 30.6 |
| GLYCERIN | 15 | 5 | 20 | 15 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 0 |
| Appearance | n/a | n/a | n/a | 5 |
| Viscosity | n/a | n/a | n/a | 4 |
| Stability | n/a | n/a | n/a | 5 |
| Soft focus effect | n/a | 5 | 5 | 5 |

TABLE 3

Inventive cosmetic composition

| Inventive Example | GLYCERIN (1) | SUM OF DIMETHICONE, DIMETHICONE CROSSPOLYMER, AND CETYL PEG/PPG-10/1 DIMETHICONE (2) | ETHYLHEXYL PALMITATE (3) | (1):(2) | (2):(3) | (1):(3) |
|---|---|---|---|---|---|---|
| 1 | 5 | 18 | 5 | 1:3.6 | 3.6:1 | 1:1 |
| 2 | 20 | 42 | 5 | 1:2.1 | 8.4: | 4:1 |
| 3 | 12.5 | 18 | 2.5 | 1:1.44 | 7.2:1 | 5:1 |
| 4 | 5 | 18 | 2.5 | 1:3.6 | 7.2:1 | 2:1 |
| 5 | 15 | 32.7 | 4 | 1:2.18 | 8.4:1 | 3.8:1 |
| 6 | 5 | 18 | 5 | 1:3.6 | 3.6:1 | 1:1 |
| 7 | 20 | 18 | 5 | 1:0.9 | 3.6:1 | 4:1 |
| 8 | 15 | 32.7 | 4 | 1:2.18 | 8.2:1 | 3.8:1 |

Inventive cosmetic compositions 1-8 are described above in Tables 1-3, wherein the ratio of glycerin and the mixture of dimethicone, dimethicone crosspolymer, and cetyl peg/ppg-10/1 is from 1:0.9 to 1:3.6, the ratio of the mixture of dimethicone, dimethicone crosspolymer, and cetyl peg/ppg-10/1 and ethylhexyl palmitate is from 3.6:1 to 8.4:1, and the ratio of glycerin and ethylhexyl palmitate is from 1:1 to 5:1, wherein the ratio of glycerin and the mixture of dimethicone, dimethicone crosspolymer, and cetyl peg/ppg-10/1 excludes 1:1.5, and wherein the ratio of glycerin and ethylhexyl palmitate excludes 2.5:1.

TABLE 4

Comparative cosmetic composition

| Formulas | Comparative Example 1 | Comparative Example 2 | Comparative Example 3 | Comparative Example 4 |
|---|---|---|---|---|
| POLYSILICONE-11 | 2 | 2 | 2 | 2 |
| DIMETHICONE; 5cs | 10 | 6 | 10 | 10 |
| DIMETHICONE CROSSPOLYMER; DOW CORNING EL-9240 SILICONE ELASTOMER BLEND 2cs | 17.5 | 10.5 | 17.5 | 17.5 |
| CETYL PEG/PPG-10/1 DIMETHICONE; ABIL EM90 | 2.5 | 1.5 | 2.5 | 2.5 |
| ETHYLHEXYL PALMITATE | 5 | 5 | 2.5 | 2.5 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 34.8 | 39.3 | 44.8 | 37.3 |
| GLYCERIN | 12.5 | 20 | 5 | 12.5 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 4 | 4 | 5 | 5 |
| Viscosity | 4 | 4 | 3 | 2 |
| Stability | 5 | 5 | 5 | 5 |
| Soft focus effect | n/a | n/a | n/a | n/a |

TABLE 5

Comparative cosmetic composition

| Formulas | Comparative Example 5 | Comparative Example 6 | Comparative Example 7 |
|---|---|---|---|
| POLYSILICONE-11 | 2 | 2 | 2 |
| DIMETHICONE; 5cs | 14 | 6 | 10 |
| DIMETHICONE CROSSPOLYMER DOW CORNING EL-9240 SILICONE ELASTOMER BLEND 2cs | 24.5 | 10.5 | 17.5 |
| CETYL PEG/PPG-10/1 DIMETHICONE; ABIL EM90 | 3.5 | 1.5 | 2.5 |
| ETHYLHEXYL PALMITATE | 2.5 | 2.5 | 0 |
| HYDROLYZED HYALURONIC ACID | 0.1 | 0.1 | 0.1 |
| DIMETHICONE (and) DIMETHICONE/VINYL DIMETHICONE CROSSPOLYMER | 0 | 0 | 0 |
| METHYL METHACRYLATE CROSSPOLYMER | 0 | 0 | 0 |
| plastic powder | 0 | 0 | 0 |
| SILICA SILYLATE | 0 | 0 | 0 |
| VINYL DIMETHICONE/METHICONE SILSESQUIOXANE CROSSPOLYMER | 0 | 0 | 0 |
| ASCORBIC ACID | 10.5 | 10.5 | 10.5 |
| ASCORBYL GLUCOSIDE | 2 | 2 | 2 |
| PROPYLENE GLYCOL | 32.8 | 41.8 | 32.3 |
| GLYCERIN | 5 | 20 | 20 |
| HYDROXYETHYLPIPERAZINE ETHANE SULFONIC ACID | 1 | 1 | 1 |
| ADENOSINE | 0.1 | 0.1 | 0.1 |
| *ANOGEISSU LEIOCARPUS* BARK EXTRACT | 2 | 2 | 2 |
| Appearance | 4 | 4 | 5 |
| Viscosity | 3 | 3 | 2 |
| Stability | 5 | 5 | 5 |
| Soft focus effect | n/a | n/a | n/a |

TABLE 6

Comparative cosmetic composition

| Formulas | Comparative Example 8 | Comparative Example 9 | Comparative Example 10 | Comparative Example 11 |
|---|---|---|---|---|
| POLYSILICONE-11 | 2 | 2 | 2 | 2 |
| DIMETHICONE; 5cs | 12 | 6 | 10.5 | 6 |
| DIMETHICONE CROSSPOLYMER; DOW CORNING EL-9240 SILICONE ELASTOMER BLEND 2cs | 21 | 10.5 | 1.5 | 10.5 |
| CETYL PEG/PPG-10/1 DIMETHICONE; ABIL EM90 | 3 | 1.5 | 6 | 1.5 |
| ETHYLHEXYL PALMITATE | 0 | 0 | 0 | 0 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 39.3 | 59.3 | 44.3 | 51.8 |
| GLYCERIN | 7 | 5 | 20 | 12.5 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 5 | 5 | 5 | 5 |
| Viscosity | 1 | 1 | 1 | 1 |
| Stability | 5 | 5 | 5 | 5 |
| Soft focus effect | n/a | n/a | n/a | n/a |

TABLE 7

Comparative cosmetic composition

| Formulas | Comparative Example 12 | Comparative Example 13 | Comparative Example 14 | Comparative Example 15 |
|---|---|---|---|---|
| POLYSILICONE-11 | 2 | 2 | 2 | 2 |
| DIMETHICONE; 5cs | 10 | 10 | 14 | 14 |
| DIMETHICONE CROSSPOLYMER; DOW CORNING EL-9240 SILICONE ELASTOMER BLEND 2cs | 17.5 | 17.5 | 24.5 | 24.5 |
| CETYL PEG/PPG-10/1 DIMETHICONE; ABIL EM90 | 2.5 | 2.5 | 3.5 | 3.5 |
| ETHYLHEXYL PALMITATE | 5 | 0 | 5 | 2.5 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 42.3 | 39.8 | 22.8 | 25.3 |
| GLYCERIN | 5 | 12.5 | 12.5 | 12.5 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 4 | 4 | 3 | 3 |
| Viscosity | 2 | 1 | 5 | 5 |
| Stability | 5 | 5 | 2 | 2 |
| Soft focus effect | n/a | n/a | n/a | n/a |

TABLE 8

Comparative cosmetic composition

| Formulas | Comparative Example 16 | Comparative Example 17 | Comparative Example 18 | Comparative Example 19 |
|---|---|---|---|---|
| POLYSILICONE-11 | 2 | 2 | 2 | 2 |
| DIMETHICONE; 5cs | 10 | 14 | 14 | 10 |
| DIMETHICONE CROSSPOLYMER; DOW CORNING EL-9240 SILICONE ELASTOMER BLEND 2cs | 17.5 | 24.5 | 24.5 | 17.5 |
| CETYL PEG/PPG-10/1 DIMETHICONE; ABIL EM90 | 2.5 | 3.5 | 3.5 | 2.5 |
| ETHYLHEXYL PALMITATE | 2.5 | 2.5 | 5 | 5 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYL METHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 29.8 | 17.8 | 30.3 | 27.3 |
| GLYCERIN | 20 | 20 | 5 | 20 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 4 | 3 | 3 | 3 |
| Viscosity | 4 | 5 | 5 | 5 |
| Stability | 2 | 2 | 2 | 2 |
| Soft focus effect | n/a | n/a | n/a | n/a |

TABLE 9

Comparative cosmetic composition

| Formulas | Comparative Example 20 | Comparative Example 21 | Comparative Example 22 | Comparative Example 23 |
|---|---|---|---|---|
| POLYSILICONE-11 | 2 | 2 | 0 | 0 |
| DIMETHICONE; 5cs | 6 | 14 | 6 | 6.75 |
| DIMETHICONE CROSSPOLYMER; DOW CORNING EL-9240 SILICONE ELASTOMER BLEND 2cs | 10.5 | 24.5 | 10.5 | 8 |
| CETYL PEG/PPG-10/1 DIMETHICONE; ABIL EM90 | 1.5 | 3.5 | 1.5 | 1.5 |
| ETHYLHEXYL PALMITATE | 5 | 0 | 5 | 5 |
| HYDROLYZED HYALURONIC ACID | 0.1 | 0.1 | 0.1 | 0.1 |
| DIMETHICONE (and) DIMETHICONE/VINYL DIMETHICONE CROSSPOLYMER | 0 | 0 | 0 | 0 |
| METHYLMETHACRYLATE CROSSPOLYMER | 0 | 0 | 0 | 0 |
| plastic powder | 0 | 0 | 0 | 0 |
| SILICA SILYLATE | 0 | 0 | 0 | 0 |
| VINYL DIMETHICONE/METHICONE SILSESQUIOXANE CROSSPOLYMER | 0 | 0 | 0 | 0 |
| ASCORBIC ACID | 10.5 | 10.5 | 10.5 | 10.5 |
| ASCORBYL GLUCOSIDE | 2 | 2 | 2 | 2 |
| PROPYLENE GLYCOL | 46.8 | 20.3 | 56.3 | 47.15 |
| GLYCERIN | 12.5 | 20 | 5 | 15.9 |
| HYDROXYETHYLPIPERAZINE ETHANE SULFONIC ACID | 1 | 1 | 1 | 1 |
| ADENOSINE | 0.1 | 0.1 | 0.1 | 0.1 |
| *ANOGEISSUS LEIOCARPUS* BARK EXTRACT | 2 | 2 | 2 | 2 |
| Appearance | 3 | 4 | n/a | n/a |
| Viscosity | 4 | 3 | n/a | n/a |
| Stability | 2 | 2 | n/a | n/a |
| Soft focus effect | n/a | n/a | 4 | 4 |

TABLE 10

Comparative cosmetic composition

| Formulas | Comparative Example 24 | Comparative Example 25 | Comparative Example 26 |
|---|---|---|---|
| POLYSILICONE-11 | 0 | 0 | 0 |
| DIMETHICONE; 5cs | 6 | 6 | 6 |
| DIMETHICONE CROSSPOLYMER; DOW CORNING EL-9240 SILICONE ELASTOMER BLEND 2cs | 10.5 | 10.5 | 10.5 |
| CETYL PEG/PPG-10/1 DIMETHICONE; ABIL EM90 | 1.5 | 1.5 | 1.5 |
| ETHYLHEXYL PALMITATE | 5 | 5 | 5 |
| HYDROLYZED HYALURONIC ACID | 0.1 | 0.1 | 0.1 |
| DIMETHICONE (and) DIMETHICONE/VINYL DIMETHICONE CROSSPOLYMER | 2 | 0 | 0 |
| METHYL METHACRYLATE CROSSPOLYMER | 0 | 2 | 0 |
| plastic powder | 0 | 0 | 2 |
| SILICA SILYLATE | 0 | 0 | 0 |
| VINYL DIMETHICONE/METHICONE SILSESQUIOXANE CROSSPOLYMER | 0 | 0 | 0 |
| ASCORBIC ACID | 10.5 | 10.5 | 10.5 |
| ASCORBYL GLUCOSIDE | 2 | 2 | 2 |
| PROPYLENE GLYCOL | 54.3 | 54.3 | 54.3 |
| GLYCERIN | 5 | 5 | 5 |
| HYDROXYETHYLPIPERAZINE ETHANE SULFONIC ACID | 1 | 1 | 1 |
| ADENOSINE | 0.1 | 0.1 | 0.1 |
| *ANOGEISSUS LEIOCARPUS* BARK EXTRACT | 2 | 2 | 2 |
| CYCLOPENTASILOXANE | 0 | 0 | 0 |
| CYCLOPENTASILOXANE (and) DIMETHICONE CROSSPOLYMER | 0 | 0 | 0 |
| Appearance | n/a | n/a | n/a |
| Viscosity | n/a | n/a | n/a |

TABLE 10-continued

Comparative cosmetic composition

| Formulas | Comparative Example 24 | Comparative Example 25 | Comparative Example 26 |
|---|---|---|---|
| Stability | 4 | 4 | n/a |
| Soft focus effect | n/a | n/a | 5 |

TABLE 11

Comparative cosmetic composition

| Formulas | Comparative Example 27 | Comparative Example 28 | Comparative Example 29 |
|---|---|---|---|
| POLYSILICONE-11 | 0 | 0 | 0 |
| DIMETHICONE; 5cs | 6 | 6 | 0 |
| DIMETHICONE CROSSPOLYMER; DOW CORNING EL-9240 SILICONE ELASTOMER BLEND 2cs | 10.5 | 10.5 | 0 |
| CETYL PEG/PPG-10/1 DIMETHICONE; ABIL EM90 | 1.5 | 1.5 | 13 |
| ETHYLHEXYL PALMITATE | 5 | 5 | 0 |
| HYDROLYZED HYALURONIC ACID | 0.1 | 0.1 | 0 |
| DIMETHICONE (and) DIMETHICONE/VINYL DIMETHICONE CROSSPOLYMER | 0 | 0 | 0 |
| METHYL METHACRYLATE CROSSPOLYMER | 0 | 0 | 0 |
| plastic powder | 0 | 0 | 0 |
| SILICA SILYLATE | 2 | 0 | 0 |
| VINYL DIMETHICONE/METHICONE SILSESQUIOXANE CROSSPOLYMER | 0 | 2 | 0 |
| ASCORBIC ACID | 10.5 | 10.5 | 10.5 |
| ASCORBYL GLUCOSIDE | 2 | 2 | 0 |
| PROPYLENE GLYCOL | 54.3 | 54.3 | 45.96 |
| GLYCERIN | 5 | 5 | 7 |
| HYDROXYETHYLPIPERAZINE ETHANE SULFONIC ACID | 1 | 1 | 0 |
| ADENOSINE | 0.1 | 0.1 | 0 |
| *ANOGEISSUS LEIOCARPUS* BARK EXTRACT | 2 | 2 | 0 |
| CYCLOPENTASILOXANE | 0 | 0 | 15.5 |
| CYCLOPENTASILOXANE (and) DIMETHICONE CROSSPOLYMER | 0 | 0 | 18 |
| Appearance | n/a | n/a | 5 |
| Viscosity | n/a | n/a | 4 |
| Stability | n/a | n/a | 2 |
| Soft focus effect | 2 | 3 | n/a |

In some embodiments, a formulation made generally in accordance with the method described above may have 0.2-0.3 wt % of polysilicone-11, 27-28 wt % of dimethicone (5cs), 2-3 wt % of dimethicone crosspolymer, 2-3 wt % of cetyl peg/ppg-10/1 dimethicone, 3-5 wt % of ethylhexyl palmitate, 0.05-0.15 wt % of hydrolyzed hyaluronic acid, 10-11 wt % of ascorbic acid, 1-3 wt % of ascorbyl glucoside, 28-30 wt % of propylene glycol, 14-16 wt % of glycerin, 0.5-1.5 wt % of hydroxyethylpiperazine ethane sulfonic acid, and any one or more of adenosine, anogeissus leiocarpus bark extract, acrylonitrile/methyl methacrylate/vinylidene chloride copolymer, lauroyl lysine, cyclohexasiloxane, pentaerythrityl tetra-di-t-butyl hydroxyhydrocinnamate, isobutene, *citrus aurantium dulcis* (orange) peel oil and *citrus limon* (lemon) peel oil, within the weight percentage ranges as set forth in the disclosure for various such ingredients.

Raw Materials

Polysilicon-11: Commercially available under the Trade Name GRANSIL RPS-D6 from the supplier Grant Industries (87% by weight of Cyclohexasiloxane and 13% by weight of Polysilicon-11); Dimethicone Crosspolymer: Commercially available under the Trade Name DOW CORNING EL-9240 SILICONE ELASTOMER BLEND 2cs from the supplier Grant Industries (70% by weight of Dimethicone, 17% by weight of dimethicone and 13% of Dimethicone crosspolymer); Cetyl PEG/PPG-10/1 Dimethicone: Commercially available under the Trade Name ABIL EM90 from the supplier Evonik Goldschmidt (99.995% by weight of Cetyl peg/ppg-10/1 dimethicone and 0.005 by weight of Pentaerythrityl Tetra-Di-T-Butyl Hydroxyhydrocinnamate).

Evaluation of Appearance

The samples of the inventive and comparative formulations, as described above, were subject to visual (eye) observation to evaluate appearance. Score concerning appearance was set in 5 grades of "Excellent, Brilliant, Smooth (5 points); Good, Smooth (4 points); Acceptable, Slightly rough surface but acceptable (3 points); Bad, Rough surface (2 points); Not acceptable, inhomogeneous (1 point) for evaluation.

Evaluation of Viscosity

Viscosity of the samples of the inventive and comparative formulations, as described above, was measured by viscometer Rheomat R180. Viscosity was measured by spindle 3 for 10 minutes at 25° C. Viscosity was measured in the UD unit. Score concerning viscosity was set in 5 grades of "Excellent, UD<=45 (5 points); Good, 45<UD<=75 (4 points); Acceptable, 75<UD<=105 (3 points); Bad, 105<UD<=135 (2 points); Not acceptable, 135<UD (1 point) for evaluation.

Evaluation of Stability

The samples of the inventive and comparative formulations, as described above, were subject to visual (eye) observation. Stability was measured after subjecting the samples to one of conditions: a) at 45° C. for one week, b) at 25° C. for one week, and c) cycles between 20° C. and −20° C. for two days. Score concerning viscosity was set in 5 grades of "Excellent, stable after 45° C. for one week and after the cycles between 20° C. and −20° C. (5 points); Good, stable after 45° C. for one week but slightly rough surface after the cycles between 20° C. and −20° C. (4 points); Acceptable, rough surface but stable after 45° C. for one week and after the cycles between 20° C. and −20° C. (3 points); Bad, slightly separate after 45° C. for one week and/or after the cycles between 20° C. and −20° C. (2 points); No effect, separate after 45° C. for one week and/or after the cycles between 20° C. and −20° C. (1 point) for evaluation.

Evaluation of Soft Focus Effect

Soft focus effect was measured with Hazemeter BYK Hazeguard 25 microns film applied on transparent film. The films were dried for 16 hours at 25° C. Transparency and Haze were measured at least from five different areas. Transparency was calculated to be the sum of $T_{diffuse}$ and $T_{direct}$. Haze was calculated to be $(T_{diffuse}/(T_{diffuse}+T_{direct}))*100$. The higher value of Haze, the better haze effect a user can experience. Score concerning soft focus effect set in 5 grades of "Excellent, 80<=Haze; Good, 60<=Haze<80 (4 points); Acceptable, 40<=Haze<60 (3 points); Bad, 20<=Haze<40 (2 points); No effect, Haze<20 (1 point) for evaluation.

In some embodiments, among the compositions above, compositions with a score of at least 14 on the sum of three of the four tested properties (appearance, viscosity, stability, and soft focus effect) are evaluated to be inventive.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition comprising:
    a. An oil phase comprising:
        i. Polysilicone-11;
        ii. Mixture of dimethicone, dimethicone crosspolymer and cetyl peg/ppg-10/1 dimethicone;
        iii. Ethylhexyl palmitate; and
        iv. Hyaluronic acid derivative;
    b. A polyol phase comprising:
        i. Soluble ascorbic acid;
        ii. Soluble ascorbyl glucoside;
        iii. Propylene glycol;
        iv. Glycerin; and
        v. Hydroxyethylpiperazine ethane sulfonic acid; and
    wherein the cosmetic composition provides immediate soft focus and long term anti-wrinkle effect.

2. The composition of claim 1, wherein the mixture of dimethicone, dimethicone crosspolymer and cetyl peg/ppg-10/1 dimethicone has a ratio from 4:7:1 to 5:8:1.

3. The composition of claim 1, wherein the hyaluronic acid derivative is hydrolyzed hyaluronic acid.

4. The composition of claim 1, wherein the polysilicone-11 is employed in an amount of from about 0.1 to 5.0% by weight, based on the weight of the composition.

5. The composition of claim 1, wherein the mixture of dimethicone, dimethicone crosspolymer and cetyl peg/ppg-10/1 dimethicone is employed in an amount of from about 18 to 42% by weight, based on the weight of the composition.

6. The composition of claim 1, wherein the ethylhexyl palmitate is employed in an amount of from about 1.0 to 5.0% by weight, based on the weight of the composition.

7. The composition of claim 1, wherein the hyaluronic acid derivative is employed in an amount of from about 0.01 to 1.0% by weight, based on the weight of the composition.

8. The composition of claim 1, wherein the ascorbic acid is employed in an amount of from about 1.0 to 20% by weight, based on the weight of the composition.

9. The composition of claim 1, wherein the ascorbyl glucoside is employed in an amount of from about 0.1 to 5.0% by weight, based on the weight of the composition.

10. The composition of claim 1, wherein the propylene glycol is employed in an amount of from about 0.1 to 60% by weight, based on the weight of the composition.

11. The composition of claim 1, wherein the glycerin is employed in an amount of from about 0.1 to 60% by weight, based on the weight of the composition.

12. The composition of claim 1, wherein the hydroxyethylpiperazine ethane sulfonic acid is employed in an amount of from about 0.1 to 5.0% by weight, based on the weight of the composition.

13. The composition of claim 1, wherein an anogeissus leiocarpus bark extract is further employed in an amount of from about 0.1 to 5.0% by weight, based on the weight of the composition.

14. A cosmetic composition comprising:
    a. An oil phase comprising:
        i. 0.1-5.0 wt % of polysilicone-11;
        ii. 18-42 wt % of mixture of dimethicone, dimethicone crosspolymer and cetyl peg/ppg-10/1 dimethicone;
        iii. 1.0-5.0 wt % of ethylhexyl palmitate; and
        iv. 0.01-1.0 wt % of hydrolyzed hyaluronic acid;
    b. A polyol phase comprising:
        i. 0.1-20 wt % of soluble ascorbic acid;
        ii. 0.1-5.0 wt % of soluble ascorbyl glucoside;
        iii. 0.1-60 wt % of propylene glycol;
        iv. 0.1-60 wt % of glycerin; and
        v. 0.1-5.0 wt % of hydroxyethylpiperazine ethane sulfonic acid; and
    wherein the cosmetic composition provides immediate soft focus and long term anti-wrinkle effect.

15. The composition of claim 14, wherein the mixture of dimethicone, dimethicone crosspolymer and cetyl peg/ppg-10/1 dimethicone has a ratio from 4:7:1 to 5:8:1.

16. The composition of claim 14, wherein the ratio of glycerin to the mixture of dimethicone, dimethicone crosspolymer, and cetyl peg/ppg-10/1 is from 1:0.9 to 1:3.6, the ratio of the mixture of dimethicone, dimethicone crosspolymer, and cetyl peg/ppg-10/1 to ethylhexyl palmitate is from 3.6:1 to 8.4:1, and the ratio of glycerin to ethylhexyl palmitate is from 1:1 to 5:1, wherein the ratio of glycerin to the mixture of dimethicone, dimethicone crosspolymer, and cetyl peg/ppg-10/1 excludes 1:1.5, and wherein the ratio of glycerin to ethylhexyl palmitate excludes 2.5:1.

17. The composition of claim 14, wherein an anogeissus leiocarpus bark extract is further employed in an amount of from about 0.1 to 5.0% by weight, based on the weight of the composition.

18. A method of making a cosmetic composition comprising:
  a. Preparing an oil phase by mixing polysilicone-11, mixture of dimethicone, dimethicone crosspolymer and cetyl peg/ppg-10/1 dimethicone, ethylhexyl palmitate, and hyaluronic acid derivative;
  b. Preparing a polyol phase by heating and dissolving ascorbic acid, ascorbyl glucoside, propylene glycol, glycerin, and hydroxyethylpiperazine ethane sulfonic acid at 85° C.;
  c. Cooling the polyol phase;
  d. Mixing the oil phase and polyol phase; and
  e. Adding an anogeissus leiocarpus bark extract to the mixture of the oil phase and polyol phase.

* * * * *